United States Patent [19]

Glazer et al.

[11] Patent Number: 4,725,599

[45] Date of Patent: Feb. 16, 1988

[54] HETEROCYCLIC RING FUSED PYRIMIDINE-4 (3H)-ONES AS ANTICOCCIDIAL AGENTS

[75] Inventors: Edward A. Glazer, Waterford; James W. McFarland, Lyme, both of Conn.

[73] Assignee: Pfizer Inc., New York, N.Y.

[21] Appl. No.: 913,884

[22] Filed: Sep. 8, 1986

[51] Int. Cl.⁴ .............. C07D 495/04; C07D 497/04; A61K 31/505

[52] U.S. Cl. ..................... 514/258; 514/267; 544/278; 544/250; 549/71

[58] Field of Search .............. 544/278, 250, 287; 514/258, 267

[56] References Cited

U.S. PATENT DOCUMENTS

| | | | |
|---|---|---|---|
| Re. 26,833 | 3/1970 | Waletzky et al. | 424/251 |
| 2,651,632 | 9/1953 | Baker et al. | 544/284 |
| 3,318,881 | 5/1967 | Ohnacker et al. | 260/246 |
| 3,320,124 | 5/1967 | Waletzky et al. | 514/259 |
| 3,706,747 | 12/1972 | DeAngelis et al. | 260/265.5 R |
| 4,239,888 | 12/1980 | Miller | 544/314 |
| 4,376,121 | 3/1983 | Kienzle | 424/251 |
| 4,632,926 | 12/1986 | Giarda et al. | 544/287 |

FOREIGN PATENT DOCUMENTS 633910 1/1962 Canada .
1959402 6/1971 Fed. Rep. of Germany .

OTHER PUBLICATIONS

Monograph Nos. 3881 and 4479, The Merck Index, Tenth Edition.
Huddleston et al., Synthetic Communications 9 (8), 731–734 (1979).

Primary Examiner—Donald G. Daus
Assistant Examiner—Barbara Cassatt
Attorney, Agent, or Firm—Peter C. Richardson; Albert E. Frost; Robert K. Blackwood

[57] ABSTRACT

Certain trans-3-[3-(3-hydroxy-2-piperidyl)-2-oxopropyl]thieno[3,2-d]pyrimidin-4(3H)-one and furo[3,2-d]pyrimidin-4(3H)-one derivatives, a method of using same as anticoccidial agents, intermediates therefor, and a process for certain intermediates therefor.

16 Claims, No Drawings

HETEROCYCLIC RING FUSED PYRIMIDINE-4 (3H)-ONES AS ANTICOCCIDIAL AGENTS

BACKGROUND OF THE INVENTION

The present invention is concerned with certain trans-3-[3-(3-hydroxy-2-piperidyl)-2-oxopropyl]thieno-[3,2-d]pyrimidin-4(3H)-one and furo[3,2-d]pyrimidin-4(3H)-one derivatives, a method of using same as anticoccidial agents, intermediates therefor, and a process for certain intermediates therefor.

Coccidiosis, a poultry disease, is caused by several species of protozoan parasites of the genus Eimeria, such as *E. acervulina* and *E. tenella*. In particular, *E. tenella* is the causative agent of a severe and often fatal infection of the ceca of chickens which is manifested by extensive hemorrhage, accumulation of blood in the ceca and the passage of blood in the droppings. Essentially, coccidiosis is an intestinal disease which is disseminated by birds picking up the infectious organism in droppings on contaminated litter or ground. By damaging the intestinal wall, the host animal is unable to utilize its food, goes off its feed, and in untreated cases the disease terminates in either the death of the animal or the survival of unthrifty birds known commonly as "culls".

Several classes of compounds have been reported to be useful as anticoccidial agents. Among these are various 6-azauracil derivatives (Miller, U.S. Pat. No. 4,239,888; summarizing several addition classes); trans-3-[3-(3-hydroxy-2-piperidyl)-2-oxopropyl]-4(3H)-quinazolinone (febrifugine; The Merck Index, Tenth Edition, monograph No. 3881); and trans-7-bromo-6-chloro-3-[3-(3-hydroxy-2-piperidyl)-2-oxopropyl]-4(3H)-quinazolinone (halofuginone; The Merck Index, Tenth Edition, monograph No. 4479).

SUMMARY OF THE INVENTION

Although above febrifugine and halofuginone are useful as anticoccidial agents, we have determined that a number of related compounds (such as trans-3-[3-(3-hydroxy-2-piperidyl)-2-oxopropyl]thieno[3,2-d]pyrimidin-4(3H)-one; trans-3-[3-(3-hydroxy-2-piperidyl)-2-oxopropylthieno[2,3-d]pyrimidin-4(3H)-one and the 6-chloro and 6-bromo derivatives thereof; trans-3-[3-(3-hydroxy-2-piperidyl)-2-oxopropyl]thieno[3,4-d]-pyrimidine-4(3H)-one and the 7-chloro derivative thereof; and trans-8-chloro-3-[3-(3-hydroxy-2-piperidyl)-2-oxopropyl]benzofuro[3,2-d]pyrimidine) are lacking in useful anticoccidial activity in poultry. In spite of such lack of activity, we have surprisingly discovered a number of compounds, very closely related in structure, which are highly active as anticoccidial agents, as determined by their activity against *E. tenella*.

Thus the present invention is directed to anticoccidial compounds of the formula

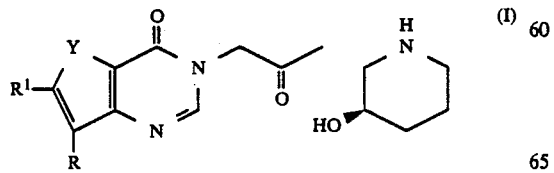

wherein
Y is sulfur or oxygen; and

R and $R^1$ are taken separately, and R is hydrogen, chloro or bromo and $R^1$ is chloro or bromo; or
R and $R^1$ are taken together and are —CH=CH—CH=CH—; with the proviso that R and $R^1$ are taken together when Y is oxygen;
including the pharmaceutically acceptable acid addition salts thereof.

The compounds of the present invention are racemic (not optically active). The heavy and dotted bonds in the various formulae therefore indicate relative, not absolute stereochemistry.

Pharmaceutically acceptable acid addition salts include, but are not restricted to, those with HCl, HBr, $H_2SO_4$, $CH_3SO_3H$, p-$CH_3C_6H_4SO_3H$, lactic acid, fumaric acid, citric acid and the like.

Preferred compound of the formula (I), because of their ease of preparation and high activity, have Y as sulfur, R and $R^1$ taken separately, $R^1$ as chloro and R as hydrogen, chloro or bromo; or Y as oxygen with R and $R^1$ taken together as —CH=CH—CH=CH—.

The present invention also encompasses a method of controlling or preventing coccidiosis in poultry which comprises administering to said poultry an anticoccidially effective amount of a compound of the formula (I) in drinking water or in nutritionally-balanced feed.

Also claimed are valuable intermediates of the formula:

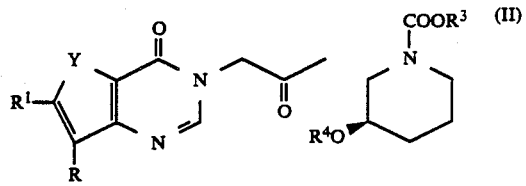

wherein
Y is sulfur or oxygen;
R and $R^1$ are taken separately, and R is hydrogen, chloro or bromo and $R^1$ is chloro or bromo; or
R and $R^1$ are taken together and are —CH=CH—CH=CH—; with the proviso that R and $R^1$ are taken together when Y is oxygen;
$R^3$ is allyl or ($C_1$-$C_4$)alkyl; and
$R^4$ is hydrogen or ($C_1$-$C_4$)alkyl;

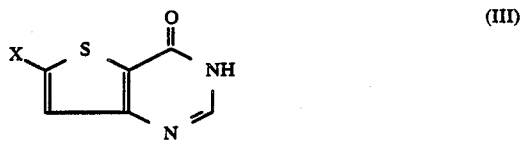

wherein X is chloro or bromo; and

wherein X is chloro or bromo and $R^2$ is ($C_1$-$C_4$)alkyl; and a process for preparation of compounds of the formula (IV) which comprises reaction of a thioglycolate ester of the formula

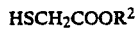

with a dihaloacrylonitrile of the formula

in a reaction inert solvent in the presence of at least one equivalent of a strong base.

As used herein, the expression "reaction inert solvent" refers to a solvent which does not interact with reagents, intermediates or products in a manner which adversely affects the yield of the desired product.

DETAILED DESCRIPTION OF THE INVENTION

The compounds of the present invention are readily prepared by nucleophilic displacement:

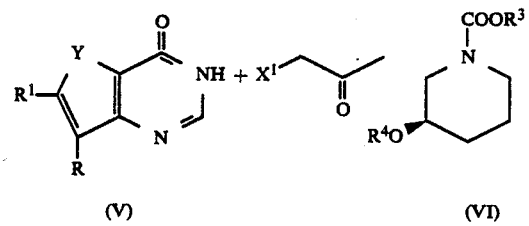

wherein R, $R^1$, $R^3$, $R^4$ and Y are as defined above, and $X^1$ is a nucleophilically displaceable group such as chloro, bromo, iodo or mesylate; followed by solvolytic or hydrolytic removal of the groups $R^4$ and $COOR^3$. Because of their ready availability, preferred compounds of the formula (VI) have $X^1$ as bromo, $R^4$ as methyl and $R^3$ as methyl or allyl.

The nucleophilic displacement reaction between compounds of the formulae (V) and (VI) in all cases involves replacement of the leaving group $X^1$ with a relatively non-nucleophilic nitrogen. For this reason it is essential to employ a base of sufficient strength to form the anion of the compound (V) in an amount at least sufficient to neutralize all of the acid ($HX^1$) coproduced in the reaction. Alkali metal ($C_1$–$C_4$)-alkoxides are well suited for this purpose. The reaction is generally carried out in a reaction inert solvent such as a lower alkanol, acetonitrile or dimethylformamide. The solvent should be less acidic than the compound (V), so as to facilitate formation of the required anion. Sodium methoxide as base in methanol as solvent represent conditions particularly well suited for the present reaction. The temperature employed for this reaction is not critical (e.g. temperatures in the range of 0°–50° C. are fully satisfactory). It should be high enough to provide a reasonable rate, but not so high as to lead to undue decomposition. As is well known in the art, rate will vary with the nature of the leaving group (e.g. rate: I>Br>Cl), the specific structure of the compound (V), the concentration of reagents and the solvent. The reaction time should be such that the reaction is nearly complete (e.g. >95% conversion when equivalent amounts of the compounds (V) and (VI) are employed) to maximize yields [e.g. reaction times 1 hour to several hours at ambient temperature are well suited when $X^1$ is bromo, the base is sodium methoxide, the solvent is methanol, and the concentration of compound (V) is in the range 3–10% (w/v)]. Of course, complete reaction can be facilitated by use of an excess of one of the reagents, e.g. an excess of the compound (VI) when it is the more readily available of the two reagents.

The present nucleophilic displacement reactions produce compounds of the above formula (II) wherein $R^4$ is ($C_1$–$C_4$)alkyl. The groups $R^4$ and $COOR^3$ are readily removed, stepwise or in a single step, to produce the desired compounds of the formula (I). Thus the ($C_1$–$C_4$)alkyl ether group is conveniently removed by the action of $BBr_3$ in a reaction inert solvent at a temperature ranging from $-70°$ to $0°$ C. Methylene chloride as solvent is particularly well suited for this purpose, since solutions of $BBr_3$ therein are commercially available. This method produces intermediate compounds of the formula (II) wherein $R^4$ is hydrogen. The $COOR^3$ group is then conveniently removed from the latter intermediates by briefly heating with concentrated aqueous HBr, e.g. heating in 48% HBr for 2 to 10 minutes at 80°–150° C., or concentrated HBr in glacial acetic acid at ambient temperature.

Alternatively, both groups $R^4$ as ($C_1$–$C_4$)alkyl and $COOR^3$ are removed in a single step by somewhat more prolonged heating in said concentrated aqueous HBr, e.g. in 48% HBr at 110° to 150° C. for 10 to 30 minutes.

The acid addition salts of the compounds of the present invention, if not directly isolated, for example, as the hydrobromide salt directly from the reaction mixture, are obtained by contacting the free base with at least one equivalent of the appropriate acid in a reaction inert solvent. Those salts which do not precipitate directly are isolated by concentration and/or the addition of a non-solvent. Conversely, the free base form is conveniently formed from an acid addition salt by neutralization of the latter in water with recovery of the free base by filtration or extraction into a water immiscible organic solvent.

The required starting compounds of the formula (VI) are known or prepared by methods well known in the chemical art. Some of the required starting compounds of the formula (V) are also known, or accessible by known methods. Others, particularly those of the above formula (III) were not practically accessible prior to the presently discovered novel process for preparing the above precursor compounds of the formula (IV). This novel process involves unprecedented reaction of 3,3-dichloro(or dibromo)acrylonitrile with the anion of a ($C_1$–$C_4$)alkyl thioglycolate. In hindsight, it is believed that this reaction occurs by the following pathway:

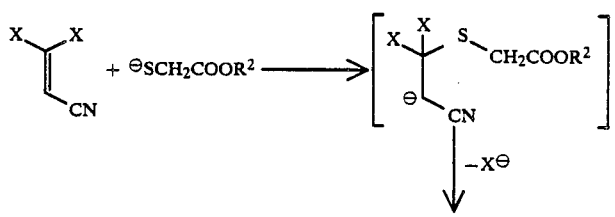

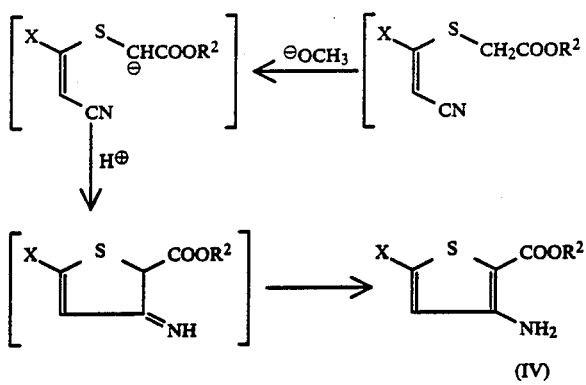

(IV)

The reaction is generally carried out under anhydrous conditions in a reaction inert solvent in the presence of at least two equivalents of a strong base. Preferred are an alkali metal ($C_1$-$C_4$)alkoxide and a solvent comprising a ($C_1$-$C_4$)alkanol. With the methyl ester (the preferred value of $R^2$), sodium methoxide as base and methanol as solvent are particularly well suited, avoiding any complications resulting from ester exchange. Temperature is not critical, but is preferably in the range 0°–50° C. Conveniently, ambient temperature is employed, with cooling as necessary to avoid any undue exotherm.

The precursor (IV) is converted to the halopyrimidine derivative (III) by standard methods, e.g. heating with excess formamide at 175° to 225° C. for several hours. Additional dihalopyrimidine derivatives of the type (III) are most conveniently obtained by halogenation of said monohalo compounds of the formula (III). For example, 7-bromo-6-chlorothieno[3,2-d]-pyrimidin-4(3H)-one is prepared from the compound (III) wherein X is chloro by treatment with $Br_2$ in acetic acid at 80° C., as specifically described below.

The cocciodiostatic activity of the compounds of the present invention is demonstrated as follows. Groups of chicks (e.g. groups of five ten-day old SPF white Leghorn cockerels) are fed a nutritionally complete basal ration into which the test compound is incorporated at various concentrations. The basal ration is generally a commercial chick starter (e.g. Agway Commercial Chick Starter, available from the Agway Feed Co., Franklin, Connecticut), and is presented ad libitum to the chicks 24 hours before infection and continuously thereafter throughout the course of the tests.

Twenty-four hours after initiation of the medication the chicks are inoculated orally with 100,000 sporulated oocysts (Eimeria tenella) and the average weight per bird per group determined. In addition, a group of six chicks is fed the basal ration which contains none of the test compound (infected, untreated controls). A further group of six chicks serves as uninfected, untreated controls. The chicks are examined on the fifth and sixth day post-infection for signs of hemorrhage. On the sixth day post-infection, the average body weight per bird per group is determined, the birds necropsied, the cecum examined macroscopically, and a pathology index (average degree of infection [A.D.I.]) determined. Chicks which die prior to the fifth day post-infection are considered as toxic deaths. Those which die five days post-infection or later are considered as deaths due to disease. The degree of pathologic involvement at necropsy is expressed as the average degree based on the following scheme: 0=no cecal lesions; 1=slight lesions; 2=moderate lesions; 3=severe lesions; 4=death.

The efficacy of the test compound, at a given level in feed, is judged by comparison of the pathologic index with that of the unmedicated infected controls, expressed as the ratio:

$$\frac{A.D.I. \text{ (treated group)}}{A.D.I. \text{ (infected, untreated controls)}}.$$

Against *E. tenella*, the compounds of the present invention generally show a value of said ratio no higher than 0.5 at a feed concentration no higher than 25 p.p.m. Preferred compounds of the present invention show even better ratios, as follows:

| Compound (I) | | | Ratios at Feed Concentration (ppm) | | | |
|---|---|---|---|---|---|---|
| Y | R | $R^1$ | 25 | 12.5 | 6.25 | 3.12 |
| S | H | Cl | 0.0 | 0.67 | 1.00 | 1.00 |
| S | Cl | Cl | 0.0 | 0.0 | 0.0 | 0.90 |
| S | Br | Cl | 0.0 | 0.0 | 0.0 | 0.67 |
| O | —CH=CH—CH=$CH_2$— | | 0.0 | 0.22 | 1.00 | 1.00 |

It will be noted that a ratio of 0.0 indicates 100% control of pathology due to the infection at the indicated feed concentration.

The compounds of this invention are orally administered to poultry in a suitable carrier. Conveniently, the medication is simply carried in the drinking water or in the poultry feed, so that a therapeutic dosage of the agent is ingested with the daily water or poultry ration. The agent can be directly metered into drinking water, preferably in the form of a liquid, water-soluble concentrate (such as aqueous solution of a water soluble salt) or added directly to the feed, as such, or in the form of a premix or concentrate. A premix or concentrate of therapeutic agent in a carrier is commonly employed for the inclusion of the agent in the feed. Suitable carriers are liquid or solid, as desired, such as water, various meals; for example, soybean oil meal, linseed oil meal, corncob meal, and mineral mixes such as are commonly employed in poultry feeds. A particularly effective carrier is the poultry feed itself; that is, a small portion of poultry feed. The carrier facilitates uniform distribution of the active materials in the finished feed with which the premix is blended. This is important because only small proportions of the present potent agents are required. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to poultry. In such instances, the poultry are permitted to consume the usual diet. Alternatively, such concentrated supplements may be added directly to the poultry feed to produce a nutritionally balanced, finished feed containing a therapeutically effective level of one or more of the compounds of this invention. The mixtures are thoroughly blended by standard procedures, such as in a twin shell blender, to ensure homogeneity.

It will, of course, be obvious to those skilled in the art that the use levels of the compounds described herein will vary under different circumstances. Continuous low-level medication, during the growing period; that is, during the first 6 to 12 weeks for chickens, is an effective prophylatic measure. In the treatment of established infections, higher levels may be necessary to overcome the infection. The use level in feed will generally be in the range of 3 to 100 ppm. When administered in drinking water, the level which will be that which will provide the same daily dose of medication, i.e. 3 to 100 ppm, factored by the weight ratio of the average daily consumption of feed to the average daily consumption of water.

The present invention is illustrated by the following examples. However, it should be understood that the invention is not limited to the specific details of these examples.

EXAMPLE 1

Methyl trans-2-[3-(6,7-Dichloro-3,4-dihydro-4-oxothieno[3,2-d]pyrimidin-3-yl)-2-oxopropyl)-3-methoxy-1-piperidinecarboxylate Under nitrogen in a flame dried round bottom flask with magnetic stirring, a solution of 0.440 g (0.002 moles) of 6,7-dichlorothieno[3,2-d]pyrimidin-4(3H)-one [M. Robba, J- M. Lecomte, and M. Cugnon de Sevricourt, Bull. soc. chim. France, 1970, 3630–3636], 5 ml of methanol, and 2.0 ml of 1.0N sodium methoxide in methanol was treated with a solution of 0.002 moles of methyl trans-3-methoxy-2-(3-bromo-2-oxopropyl)-1-piperidinecarboxylate and 2 ml of methanol. A colorless precipitate formed almost immediately; the reaction mixture was stirred for two hours at room temperature. The solid matter was some starting thienopyrimidinone, and was filtered. The filtrate was evaporated under reduced pressure to afford a greenish oil which was chromatographed under moderate pressure ("flash" chromatography) on a column of silica gel (Woelm 32–63 micrometers, i.d. 5 cm × height 18 cm); the eluant was initially 1% ethanol in chloroform but was changed to 2% ethanol later on. There was obtained the title compound: m.p. 58°-62° C.; yield 0.270 g (30%); mass spectrum peaks at 447 (molecular ion), 415 (—32, —$CH_3OH$), 195 (parent) among others; $^{13}C$-nmr delta ($CDCl_3$) 19.05 ppm, 23.42, 39.33, 40.81, 50.53, 52.93, 53.62, 56.35, 76.01, 119.92, 121.68, 149.62, 152.19, 155.49, 157.01, 199.22; $^1H$-nmr ($CDCl_3$) delta 3.36 ppm ($OCH_3$), 3.66 ($CO_2CH_3$) among others.

EXAMPLE 2

Methyl trans-2-[3-(6,7-Dichloro-3,4-dihydro-4-oxothieno[3,2-d]pyrimidin-3-yl)-2-oxopropyl]-3-hydroxy-1-piperidinecarboxylate A 35 ml single neck round bottom flask equipped with a magnetic stirring bar was flame dried and then stoppered with a serum cap. Through a syringe needle the flask was evacuated and filled with dry nitrogen four times. A solution of 0.270 g (0.0006 mole) of methyl trans-2-[3-(6,7-dichloro-3,4-dihydro-4-oxothieno[3,2-d]pyrimidin-3-yl)-2-oxopropyl]-3-methoxy-1-piperidinecarboxylate and 10 ml of dichloromethane was injected into the reaction flask, and with stirring the temperature was lowered to −70° C. Again with a syringe 3.0 ml of 1.0M boron tribromide in dichloromethane (Aldrich Chemical Co.) was introduced into the reaction vessel. After 10 minutes the reaction temperature was allowed to rise to −10° C. and was held there for 150 minutes. There was then added 11 ml of saturated aqueous sodium bicarbonate to the reaction mixture. A small amount of solid matter was filtered, and the layers of the filtrate were separated. The aqueous phase was extracted three times with 5 ml portions of dichloromethane. The extracts were combined with the organic layer, dried over anhydrous magnesium sulfate, and evaporated under reduced pressure to furnish the title compound as an off white solid: yield 0.190 g (73%); mass spectrum peaks 434 (molecular ion), 415 (—1, —18, —H, —$H_2O$), 195, 126 (parent) among others; $^1H$-nmr ($CDCl_3$) delta 1.2–2.0 ppm (multiplet, 4H, $OCHCH_2CH_2CH_2N$), 2.85 (doublet, 2H, $COCH_2CH$), 3.0 (broad triplet, 2H, $NCH_2$), 3.7 (singlet 3H, $CO_2CH_3$), 3.9–4.0 (multiplet, 2H, $CH_2CHNCO$ and OH), 4.7 (triplet with fine splitting, 1H, $\underline{C}HOCH_3$), 4.9–5.2 (multiplet, 2H, $NCH_2CO$), 8.1 (singlet, 1H, N=$\underline{CH}$—N).

EXAMPLE 3 trans-6,7-Dichloro-3-[3-(3-hydroxy-2-piperidyl)-2-oxopropyl]thieno[3,2-d]pyrimidin-4(3H)-one Dihydrobromide In a 15 ml single-neck round bottom flask equipped with a reflux condenser, a solution of 0.190 g (0.00044 mole) of methyl trans-2-[3-(6,7-dichloro-3,4-dihydro-4-oxothieno[3,2-d]pyrimidin-3-yl)-2-oxopropyl]-3-hydroxy-1-piperidinecarboxylate and 6.2 ml of 48% aqueous hydrobromic acid was immersed in an oil bath preheated to 150° C. Heating was continued for three minutes. The solution was allowed to cool to room temperature, and the volatile components were evaporated under reduced pressure. Ethanol (5 ml) was added to the residue, and again the mixture was evaporated to dryness. This operation was repeated once more to afford a dark residue which was then taken up in 3 ml of ethanol. After standing overnight at room temperature, the solution was diluted with 1 ml of ethanol and then heated at reflux briefly. Upon cooling a greyish solid precipitated. The mother liquor was removed by means of a pipette, and the residue was dried in a vacuum oven at 55° C. for 45 minutes to furnish the title compound: yield 0.080 g (48%); mass spectrum peaks at 357 (molecular ion - 18), 155, 137 (parent peak) amongst others; $^1$H-nmr (CF$_3$CO$_2$H) delta 1.3-2.0 ppm (multiplet, 4H, OCHCH$_2$CH$_2$CH$_2$N), 2.8-3.4 (multiplet, 6H, COCH$_2$CH, NCH$_2$, NCHCH$_2$, C$\underline{\text{H}}$OH), 3.7 (singlet, 1H, O$\underline{\text{H}}$), 4.9 (singlet 2H, NCH$_2$CO), 8.3 (broad singlet, 1H, N=C$\underline{\text{H}}$—N).

EXAMPLE 4

Allyl trans-2-[3-(6-chloro-3,4-dihydro-4-oxothieno[3,2-d]pyrimidin-3-yl)-2-oxopropyl]-3-methoxy-1-piperidinecarboxylate Under a nitrogen atmosphere in a flame dried flask and with magnetic stirring, a solution of 0.80 g (0.0043 mole) of 6-chlorothieno[3,2-d]pyrimidin-4(3H)-one, 3.52 ml of 1.22N sodium methoxide in methanol, and 20 ml of methanol was treated with 1.86 g (0.0056 mole) of allyl trans-3-methoxy-2-(3-bromo-2-oxopropyl)-1-piperidinecarboxylate. The reaction mixture was stirred overnight at room temperature, and was then evaporated under reduced pressure. The residue was taken up in 25 ml of 0.1N aqueous sodium hydroxide, and the resulting solution was extracted with dichloromethane. The extract was dried over anhydrous magnesium sulfate, filtered, and evaporated to afford a solid material which was chromatographed under moderate pressure ("flash" chromatography) on a column of silica gel (Woelm 32-63 micrometers, i.d. 2 cm×height 25 cm); the eluant was 7% ethanol in chloroform; after a forerun of 125 ml, 25 ml fractions were taken. Fractions 13-20 were combined and evaporated to furnish the title compound: yield 0.56 g (27%); $^1$H-nmr (CDCl$_3$) delta ppm 1.2-2.1 (multiplet, 4H, OCHCH$_2$CH$_2$CH$_2$N), 2.7-3.1 (multiplet, peaks, 4H, COCH$_2$CH and NCH$_2$), 3.3 (broad singlet, 1H, CH$_2$CHNCO), 3.4 (singlet, 3H, OCH$_3$), 4.0 (broad doublet, 1$\underline{\text{H}}$, C$\underline{\text{H}}$OCH$_3$), 4.6 (broad double, 2H, CH$_2$CH=CH$_2$), 4.8-5.1 (multiple peaks, 2H, NCH$_2$CO), 5.3 (triplet with fine splitting, 2H, CH$_2$=CH), 5.9 (octet, 1H, C$\underline{\text{H}}$=CH$_2$), 7.2 (singlet, 1H, thieno H), 8.0 (broad singlet, 1H, N=C$\underline{\text{H}}$—N).

EXAMPLE 5

Allyl trans-2-3-(6-Chloro-3,4-dihydro-4-oxothieno[3,2-d]pyrimidin-3-yl)-2-oxopropyl]-3-hydroxy-1-piperidinecarboxylate According to the method of Example 2, 0.885 g (0.0017 mole) of allyl trans-2-[3-[6-chloro-3,4-dihydro-4-oxothieno[3,2-d]pyrimidin-3-yl)-2-oxopropyl]-3-methoxy-1-piperidinecarboxylate was converted into the title compound as a white solid: $^1$H-nmr (CDCl$_3$-CD$_3$OD) delta 1.2-2.1 ppm (multiplet, 4H, OCHCH$_2$CH$_2$CH$_2$N), 2.8-3.1 (multiplet 4H, COCH$_2$CH and NCH$_2$), 3.85 (broad singlet, 1H, C$\underline{\text{H}}$NCO), 4.6 (doublet, 2H, CH$_2$—CH=CH$_2$), 4.7 (broad triplet, 1H, C$\underline{\text{H}}$OH), 5.0-5.4 (multiplet, 4H, NCH$_2$CO and CH=CH$_2$), 5.8-6.0 (octet, 1H, CH$_2$CH=CH$_2$), 7.25 (singlet, 1H, thieno H), 8.15 (singlet, 1H, N=CHN).

EXAMPLE 6 trans-6-Chloro-3-[3-(3-hydroxy-2-piperidyl)-2-oxopropyl]thieno[3,2-d]pyrimidin-4(3H)-one Dihydrobromide In a 15 ml single-neck round bottom flask equipped with a reflux condenser, a solution of 0.69 g (0.00162 mole) of allyl trans-2-[3-(6-chloro-3,4-dihydro-4-oxothieno[3,2-d]pyrimidin-3-yl)-2-oxopropyl]-3-hydroxy-1-piperidinecarboxylate and 6 ml of 48% aqueous hydrobromic acid was immersed in an oil bath preheated to 100° C. Heating was continued for 7.0 minutes. The solution was allowed to cool to room temperature, and the volatile components were evaporated under reduced pressure. Ethanol (5 ml) was added to the residue, and again the mixture was evaporated to dryness. This operation was repeated once more to afford a dark residue which was then triturated with a 1:1 solution of ethanol and acetone to furnish cream colored solid. The mixture was filtered, and the residue was dried under reduced pressure (about 1 mm Hg) to give the title compound: yield 0.50 g (61%); $^1$H-nmr (DMSO-d$_6$) delta 1.3-2.0 ppm (multiplet, 4H, OCHCH$_2$CH$_2$CH$_2$N), 2.8-3.0 (multiplet, 2H, COCH$_2$CH), 3.1-3.6 (multiplet, 4H, NCH$_2$, NCHCH$_2$, C$\underline{\text{H}}$OH), 5.2 (singlet, 2H, NCH$_2$CO), 7.6 (singlet, 1H, thieno H), 8.4 (singlet, 1H, N=C$\underline{\text{H}}$—N), 8.8 (broad singlet, 3H, NH$_2$, N$\underline{\text{H}}$).

EXAMPLE 7

Allyl trans-2-[3-(7-Bromo-6-chloro-3,4-dihydro-4-oxothieno[3,2-d]pyrimidin-3-yl)-2-oxopropyl]-3-methoxy-1-piperidinecarboxylate According to the method of Example 4, 0.662 g (0.0025 mole) of 7-bromo-6-chlorothieno[3,2-d]pyrimidin-4(3H)-one and 1.24 g (0.0037 mole) of allyl trans-3-methoxy-2-(3-bromo-2-oxopropyl)-1-piperidinecarboxylate were combined to give the title compound: yield 0.90 g (69%); $^1$H-nmr (CDCl$_3$) delta 1.3-2.1 ppm (multiplet, 4H, OCHCH$_2$CH$_2$CH$_2$N), 2.7-3.1 (multiplet, 4H, COCH$_2$CH and NCH$_2$), 3.3 (broad singlet, 1H, CH$_2$CHNCO), 3.4 (singlet, 3HOCH$_3$), 4.0 (broad doublet, 1H, C$\underline{\text{H}}$OCH$_3$), 4.6 (broad doublet, 2H, CH$_2$CH=CH$_2$), 4.9-5.1 (multiple peaks, 2H, NCH$_2$CO), 5.3 (triplet with fine splitting, 2H, CH$_2$=CH), 5.9 (octet, 1H, CH=CH$_2$), 7.2 [singlet, 0.15H, thieno H (some of the 6-chloro analog, an impurity)], 8.0 [broad singlet, 0.15H, (N=CH—N from the 6-chloro analog)], 8.1 (broad singlet, 1$\underline{\text{H}}$, N=C$\underline{\text{H}}$—N).

EXAMPLE 8

Allyl trans-2-[3-(7-Bromo-6-chloro-3,4-dihydro-4-oxothieno[3,2-d]pyrimidin-3-yl)-2-oxopropyl]-3-hydroxy-1-piperidinecarboxylate According to the method of Example 2, 0.885 g (0.0017 mole) of allyl trans-2-[3-(7-bromo-6-chloro-3,4-dihydro-4-oxothieno[3,2-d]pyrimidin-3-yl)-2-oxopropyl]-3-methoxy-1-piperidinecarboxylate was converted into the title compound: yield 0.74 g (86%); $^1$H-nmr (CDCl$_3$) delta 1.4-2.2 ppm (multiplet, 4H, OCH$_2$CH$_2$CH$_2$N), 2.7-3.2 (multiplet 2H, NCH$_2$), 2.9 (doublet, 2H COCH$_2$CH), 3.9 (broad singlet, 1H, C$\underline{\text{H}}$NCO), 4.6 (doublet, 2H, CH$_2$—CH=CH$_2$), 4.7 (broad triplet, 1H, C$\underline{\text{H}}$OH), 5.0-5.4 (multiplet, 4H, NCH$_2$CO and CH=CH$_2$), 5.8-6.0 (octet, 1H, CH$_2$CH=CH$_2$), 7.55 [singlet, 0.1H, thieno H (from the 6-chloro analog, an impurity)], 8.2 (singlet, 1H, N=C$\underline{H}$—N).

EXAMPLE 9 trans-7-Bromo-6-chloro-3-[3-(3-hydroxy-2-piperidyl)-2-oxopropyl]thieno[3,2-d]pyrimidin-4(3H)-one Dihydrobromide According to the method of Example 6, 0.68 g (0.00135 mole) of allyl trans-2-[3-(7-bromo-6-chloro-3,4-dihydro-4-oxothieno[3,2-d]pyrimidin-3-yl)-2-oxopropyl]-3-hydroxy-1-piperidinecarboxylate was transformed into the title compound: yield 0.54 g (69%); $^1$H-nmr (DMSO-d$_6$) delta 1.4–2.0 ppm (multiplet, 4H, OCHCH$_2$CH$_2$CH$_2$N), 2.8–3.0 (multiplet, 2H, COCH$_2$CH), 3.1–3.6 (multiplet, 4H, CH$_2$N, CHOH, CH$_2$CHN), 5.2 (singlet, 2H, NCH$_2$CO), 7.6 [singlet, 0.1H, thieno H (from the 6-chloro analog, an impurity)], 8.3 [singlet, 0.1H, N=C$\underline{H}$—N (from the 6-chloro analog)], 8.45 (singlet, 1H, N=C$\underline{H}$—N), 8.7 (broad singlet, 3H, NH$_2$, N$\underline{H}$).

EXAMPLE 10

Methyl trans-2-[3-(3,4-dihydro-4-oxobenzofuro[3,2-d]pyrimidin-3-yl)-2-oxopropyl]3-methoxy-1-piperidinecarboxylate According to the method of Example 1, 1.22 g (0.0066 mole) of benzofuro[3,2-d]pyrimidin-4(3H)-one [S. S. Sangapure and Y. S. Agasimundin, Indian J. Chem., 14B, 688–691 (1976)] and 0.0066 moles of methyl trans-3-methoxy-2-(3-bromo-2-oxopropyl)-1-piperidinecarboxylate were combined to give the title compound: yield 0.627 g (23%); $^1$H-nmr (CDCl$_3$) delta 1.2–2.1 ppm (multiplet, 4H, CH$_3$OCHCH$_2$CH$_2$CH$_2$N), 2.7–3.2 (multiplet, 2H, NCH$_2$), 2.9 (doublet, 2H, COCH$_2$CH), 3.3 (singlet, 3H, CHOCH$_3$), 3.7 (singlet, 3H, CO$_2$CH$_3$), 4.0 (broad doublet, 1H C$\underline{H}$OCH$_3$), 4.9 (broad triplet, 1H, CH$_2$C$\underline{H}$NCO), 5.2 (singlet, 2H, NCH$_2$CO), 7.3–7.7 (multiplet, 3H, aromatic H), 8.0 (doublet, 1H, aromatic H), 8.2 (singlet, 1H, N=C$\underline{H}$—N).

EXAMPLE 11 trans-3-[3-(3-Hydroxy-2-piperidyl)-2-oxopropyl]benzofuro[3,2-d]pyrimidin-4(3H)-one Dihydrobromide A solution of 0.600 g (0.00145 mole) of methyl trans-2-[3-(3,4-dihydro-4-oxobenzofuro[3,2-d]pyrimidin-3-yl)-2-oxopropyl]-3-methoxy-1-piperidinecarboxylate and 30 ml of 48% hydrobromic acid in a 100 ml round bottom flask was immersed in a bath preheated to 150° C. and held there for 12 minutes. Upon cooling to room temperature, the solution was evaporated under reduced pressure to afford a residue. The residue was heated with ethanol briefly; the mixture was allowed to cool, and the ethanol removed by pipette to furnish the title compound: m.p. 257°–258° C.; yield 0.28 g (41%); $^1$H-nmr (DMSO-d$_6$) delta 1.4–2.0 ppm (multiplet, 4H, CH$_3$OCHCH$_2$CH$_2$CH$_2$N), 2.8–3.0 (multiplet, 2H, NCH$_2$), 3.1–3.5 (multiplet, includes H$_2$O, CHOH, COCH$_2$CH, and CH$_2$C$\underline{H}$NCO), 5.2 (singlet, 2H, NCH$_2$CO), 7.5 (triplet, 1$\overline{H}$, aromatic H), 7.7 (triplet, 1H, aromatic H), 7.9 (doublet, 1H, aromatic H), 8.1 (doublet, 1H, aromatic H), 8.4 (singlet, 1H, N=C$\underline{H}$—N), 8.7 (broad singlet, 1H, O$\underline{H}$).

PREPARATION 1

1-[5,6-Dihydro-6-ethoxy-1,2(4H)-oxazin-3-yl]ethanone

A 1000 ml three-neck flask equipped with a mechanical stirrer, a reflux condenser, and a nitrogen inlet adapter was heat dried and charged with nitrogen. When the flask was at room temperature, it was loaded in order: 39.5 g (0.37 mole) of anhydrous sodium carbonate; (with stirring) 132 g (1.83 mole) of ethyl vinyl ether; and (portionwise over a period of 7 minutes) 10.0 g (0.074 mole) of 1-chlorobutan-2,3-dione-2-oxime [Oglobin et al., J. Gen. Chem. U.S.S.R. 34, 2710 (1964)]. Stirring was continued for 21 hours. The reaction mixture was filtered, the solid cake rinsed with diethyl ether, and the combined filtrate and rinses were evaporated under reduced pressure (bath temperature maintained at <40° C.). There was obtained 12.4 g (98%) of the title compound as an oil; nmr spectroscopy indicated it to be essentially 100% pure. This procedure is essentially that described by T. L. Gilchrist, G. M. Iskander and A. K. Yagoub (J. Chem. Soc., Chem. Commun. 1981, 696–698).

PREPARATION 2

3-Methoxy-2-methylpyridine 1-oxide

With ice-bath cooling and mechanical stirring, a solution of 200 ml of methanol and 30 ml of 12N hydrochloric acid was treated with a stream of dry hydrogen chloride gas until it was approximately 12N by titration (1.00 ml aliquot diluted with 50 ml of water and brought to neutrality with 5.00N sodium hydroxide). With continued stirring and cooling hydrogen chloride was again led through the solution while 12.0 g (0.70 mole) of 1-[5,6-dihydro-6-ethoxy-1.2(4H)-oxazin-3-yl]ethanone was added dropwise over a period of about 15 minutes. The solution was allowed to warm to room temperature and to remain standing for three hours. The now dark red-brown solution was evaporated under reduced pressure to furnish a dark brown viscous fluid which was diluted with about 100 ml of water and adjusted to pH 8 by the addition of solid sodium bicarbonate. Some insoluble matter was filtered and rinsed with small portions of water. At this point the aqueous solution was divided into equal parts and two purification methods were used.

Method A. The aqueous solution from above was extracted six times with 25 ml portions of chloroform. The combined extracts were dried over anhydrous sodium sulfate, filtered, and evaporated under reduced pressure to afford 3.26 g (67%) of crude 3-methoxy-2-methylpyridine 1-oxide: m.p. 59°–74° C. This material was further purified by heating it under reflux in 50 ml of toluene for 15 minutes; the hot solution was decanted from a small amount of insoluble gummy matter. Upon cooling to room temperature, the toluene solution was evaporated under reduced pressure to give brownish crystals: m.p. 69°–79° C. [lit. m.p. 65° C., T. L. Gilchrist et al., loc. cit.; m.p. 64°–65° C., Y. Mizuno, T. Endo and T. Nakamura, J. Org. Chem., 40(10), 1391–1395 (1975)].

Method B. The other half of the aqueous solution from above was filtered through a pad of diatomaceous earth and activated carbon, and was then treated with 4 ml of 60% hexafluorophosphoric acid. Yellow hexagonal plates of the hemi-hexafluorophosphate salt of 3-methoxy-2-methylpyridine 1-oxide (1:2) precipitated: m.p. 161°–163.5° C.; yield 3.45 g (46%).

Analysis Calcd. for $(C_7H_9NO_2)_2 \cdot HPF_6$: C, 39.63; H, 4.51; N, 6.60%. Found: C, 39.67; H, 4.48; N, 6.64%.

To a magnetically stirred saturated aqueous solution of sodium bicarbonate was added portionwise 2.00 g of the hemi-hexafluorophosphate from above. The aqueous solution was then extracted with four 15 ml portions of chloroform. The combined extracts were dried over anhydrous sodium sulfate, filtered, and evaporated under reduced pressure to furnish 3-methoxy-2-methylpyridine 1-oxide as an off-white solid: m.p. 71°-74° C.; yield 1.17 g (89%).

PREPARATION 3

3-Methoxy-2-methylpyridine

Under a nitrogen atmosphere, a magnetically stirred solution of 25.8 g (0.185 mole) of 3-methoxy-2-methylpyridine 1-oxide and 200 ml of chloroform cooled to 0° C. was treated dropwise a solution of 75.6 g (0.556 mole) of phosphorus trichloride and 50 ml of chloroform. The temperature was maintained at <10° C. during the addition. The solution was stirred for 20 minutes after the addition was complete, was allowed to warm to room temperature, and was then heated under reflux for an hour. When again at room temperature, the solution was poured into a mixture of ice and water, and the mixture was then adjusted to pH 13 by the addition of 5N sodium hydroxide and solid sodium hydroxide while keeping the mixture cold. The organic phase was separated and the aqueous phase was extracted three times with 50 ml portions of chloroform. The combined organic phase and extracts were dried over anhydrous sodium suflate, filtered, and evaporated under reduced pressure to give 3-methoxy-2-methylpyridine as an oil: b.p. 46° C. at 1.8 mmHg; yield 21.5 g (94%). Lit. b.p. 84.5°-85.5° C. at 17 mmHg [A. L. Logothetis, J. Org. Chem., 29, 1834-1837 (1969)].

(3-Methoxy-2-pyridyl)-2-propanone was prepared from 3-methoxy-2-methylpyridine according to the procedure of Barringer et al. [D. F. Barringer, Jr., G. Berkelhammer, S. D. Carter, L. Goldman, and A. E. Lanzilotti, J. Org. Chem. 38, 1933-1937 (1973)].

cis-(3-Methoxy-2-piperidyl)-2-propanone was prepared from (3-methoxy-2-pyridyl)-2-propanone by the method of Barringer et al. (loc. cit.).

An equilibrium mixture of cis- and trans-(3-methoxy-2-piperidyl)-2-propanone was prepared by the procedure of Barringer et al. (loc. cit.).

PREPARATION 4

Methyl trans-3-Methoxy-2-(2-oxopropyl)-1-piperidinecarboxylate

In a 1 liter three-neck round bottom flask equipped with a magnetic stirrer, an internal thermometer, and a dropping funnel was placed a solution of 10 g (0.058 mole) of a mixture of cis- and trans-(3-methoxy-2-piperidyl)-2-propanone and 200 ml of chloroform. With stirring and ice-bath cooling the mixture was treated dropwise with 200 ml of saturated aqueous sodium bicarbonate, the temperature being maintained below 10° C. After the addition was complete the temperature was brought to 3° C. Methyl chloroformate (16.5 g, 13.5 ml, 0.175 mole) was then added dropwise while maintaining the temperature <7° C. Stirring and cooling was continued for 75 minutes. The layers were separated and the aqueous phase was extracted three times with 75 ml portions of chloroform. The combined organic phases were dried over anhydrous sodium sulfate, filtered, and evaporated under reduced pressure to furnish 14 g of a pale orange, clear oil. The oil was then chromatographed on a column of silica gel (Woelm 32-63 micrometers, i.d. 7 cm × height 28 cm); the eluant was toluene:ethyl acetate 2:1; 200 ml fractions were collected. Fractions 10 and 11 afforded pure methyl cis-3-methoxy-2-(2-oxopropyl)-1-piperidinecarboxylate as a colorless oil: yield 0.69 g (5%); $^1$H-nmr (CDCl$_3$) delta 2.2 ppm (COCH$_3$), 3.3 (OCH$_3$), 3.7 (CO$_2$CH$_3$) and others; $^{13}$C-nmr (CDCl$_3$) delta 23.84 ppm, 25.05, 29.93, 38.50, 39.38, 50.08, 52.67, 56.38, 77.22, 155.97. Fractions 12-14 gave an oil consisting of both stereoisomers: yield 2.7 g (19%). Fractions 15-19 furnished pure methyl trans-3-methoxy-2-(2-oxopropyl)-1-piperidinecarboxylate as a colorless oil: yield 5.36 g (37%); $^1$H-nmr (CDCl$_3$) delta 2.2 ppm (COCH$_3$), 3.4 (OCH$_3$), 3.7 (CO$_2$CH$_3$) and others; $^{13}$C-nmr (CDCl$_3$) delta 19.26 ppm, 23.70, 29.93, 39.36, 43.65, 49.45, 52.52, 56.22, 75.69, 156.42.

PREPARATION 5

Methyl trans-3-Methoxy-2-(3-bromo-2-oxopropyl)-1-piperidinecarboxylate

Under a nitrogen atmosphere with magnetic stirring at room temperature, a solution of 1.26 g (0.0055 mole) of methyl trans-3-methoxy-2-(2-oxopropyl)-1-piperidinecarboxylate and 5.0 ml of absolute methanol was treated with 0.874 g (0.282 ml, 0.0055 mole) of bromine. After about 30 minutes the solution changed from reddish-brown to colorless. The volatile components were evaporated under reduced pressure; the residue was taken up in 10 ml of dichloromethane and the new solution was evaporated again to a residue. This residue was taken up in 10 ml of carbon tetrachloride, and again the volatile components were evaporated. There was obtained 1.8 g of an oil which by nmr spectroscopy contained some 85% of the title compound; the remainder consisted of some starting material and possibly other unidentified by-products: mass spectrum 307 (molecular ion); 275 (—CH$_3$OH), 236, 228 (—Br), 196 (parent peak, —Br, —CH$_3$OH); $^{13}$C-nmr (CDCl$_3$) delta 19.22 ppm, 23.81, 33.96, 39.44, 39.71, 49.74, 52.70, 56.33, 75.71, 156.55, 199.47.

PREPARATION 6

Allyl trans-3-Methoxy-2-(3-bromo-2-oxopropyl)-1-piperidinecarboxylate

Under a nitrogen atmosphere at room temperature with magnetic stirring a solution of 11.9 g (0.07 moles) of a mixture of cis- and trans-(3-methoxy-2-piperidyl)-2-propanone, 45 ml of acetic acid and 49 ml of 33% hydrogen bromide in acetic acid was treated dropwise with a solution of 12.23 g (3.92 ml, 0.077 mole) of bromine and 13.5 ml of acetic acid. Some warming occurred during the addition. After being stirred for about two hours, the reaction solution was evaporated under reduced pressure while keeping the bath temperature at <40° C. The residue was taken up in 400 ml of chloroform. The solution was cooled to 0° C., and with stirring was treated with 400 ml of saturated aqueous sodium bicarbonate. When the temperature was again at 0° C., 27.7 g (24.4 ml, 0.23 mole) of allyl chloroformate was added over a period of one minute. The reaction mixture was stirred at 0° C. for an hour. The layers were then separated, and the aqueous phase was extracted once with 200 ml of chloroform. The combined organic phases were then washed once each with 200 ml portions of 1N hydrochloric acid and water. The chloroform solution was dried over anhydrous magnesium sulfate, filtered, and evaporated under reduced pressure to furnish 36.2 g of a red-orange oil. This material was chromatographed under moderate pressure ("flash" chromatography) on a column of silica gel (Woelm 32-63 micrometers, i.d. 7 cm × height 50 cm); the eluant was toluene:ethyl acetate 5:1. There was obtained in the early fractions 3.56 g of the cis isomer; the later fractions afforded 7.59 g (33%) of allyl trans-3-methoxy-2-(3-bromo-2-oxopropyl)-1-piperidinecarboxylate: $^{13}$C-nmr delta (CDCl$_3$) 19.25 ppm, 23.84, 34.11, 39.36, 39.62, 49.54, 56.23, 66.00, 75.57, 117.07, 132.73, 155.42, 199.07.

This material has been reported earlier in the literature except that the isolation of the trans isomer was not described and it is uncertain what the ratio of cis to trans isomers was [B. R. Baker and F. J. McEvoy, J. Org. Chem. 20, 136-142 (1955)].

PREPARATION 7

Methyl 3-Amino-5-chloro-2-thiophenecarboxylate

In a flame dried flask under a nitrogen atmosphere, and with mechanical stirring, a solution of about 1.2 g (0.05 mole) of sodium metal dissolved in 30 ml of dry methanol was treated dropwise with 2.35 g (1.98 ml, 0.022 mole) of methyl thioglycolate while maintaining the temperature below 25° C. A solution of 2.70 g (0.022 mole) of 3,3-dichloroacrylonitrile [R. L. Soulen, D. B. Clifford, F. F. Crim and J. A. Johnston, J. Org. Chem. 36 (22), 3386-3391 (1971)] and 10 ml of methanol was then added dropwise at a rate such as to keep the reaction temperature <28° C. The reaction mixture became cloudy and orange. Stirring was continued for an hour. The mixture was concentrated under reduced pressure, was diluted with water, and was extracted five times with 60 ml portions of chloroform. The combined extracts were dried over anhydrous magnesium sulfate, filtered, and evaporated under reduced pressure to furnish an oil which was chromatographed under moderate pressure ("flash" chromatography) on a column of silica gel (Woelm 32-63 micrometers, i.d. 5 cm × height 18 cm); the eluant was isopropyl ether; 15 ml fractions were taken. Fractions 15-20 were combined and evaporated to give methyl 3-amino-5-chloro-2-thiophenecarboxylate as a colorless solid: m.p. 99°-101° C.; yield 0.60 g (14%); ir (KBr) 3448 cm$^{-1}$, 3343, 1674, 1615, 1546, 1455, 1425 along others; $^1$H-nmr (CDCl$_3$) delta 3.8 ppm (s, 3H), 5.3 (broad s, 2H), 6.4 (s, 1H); mass spectrum 191 (molecular ion), 159 (−32, CH$_3$OH, parent peak) and others.

Analysis Calcd. for C$_6$H$_6$ClNO$_2$S: C, 37.60; H, 3.16; N, 7.31; S, 16.73%. Found: C, 37.71; H, 3.21; N, 7.21; S, 16.18%.

PREPARATION 8

6-Chlorothieno[3,2-d]pyrimidin-4(3H)-one

In a 50 ml round bottom flask equipped with a mechanical stirrer and a reflux condenser, a mixture of 7.0 g (0.036 mole) of methyl 3-amino-5-chloro-2-thiophenecarboxylate and 15 ml of formamide was heated at 205° C. for 7 hours. Upon cooling to room temperature, the reaction solution afforded a precipitate which was filtered: yield about 3.3 g. The crude tan solid was taken up in hot methanol, treated with activated carbon, and filtered. Upon cooling to room temperature, the filtrate afforded yellow crystals of 6-chlorothieno[3,2-d]pyrimidin-4(3H)-one: m.p. 238°-239° C.; yield 2.5 g (36%); ir (KBr) 3427 cm$^{-1}$, 1688, 1659, 1600, 1510, 1476, 1410 among others; $^1$H-nmr (CDCl$_3$+some trifluoroacetic acid) delta 7.5 ppm (s, 1H), 9.1 (s, 1H); mass spectrum 186 (molecular ion and parent peak with the expected isotope pattern), 159 (−27), 131 and others.

Analysis Calcd. for C$_6$H$_3$ClNOS: C, 38.61; H, 1.62; N, 15.01%. Found: C, 38.51; H, 1.77; N, 14.92%.

PREPARATION 9

7-Bromo-6-chlorothieno[3,2-d]pyrimidin-4(3H)-one

A solution of 1.12 g (0.006 mole) of 6-chlorothieno[3,2-d]pyrimidin-4(3H)-one and 15 ml of acetic acid at 80° C. was treated with 2.88 g (0.92 ml, 0.018 mole) of bromine. Heating was continued for 2.5 hours during which time solids precipitated. After cooling to room temperature, the mixture was filtered and washed with acetic acid, water and acetone. There was obtained 0.70 g (44%) of the title compound: m.p. above 280° C.; mass spectrum 264 (molecular ion and parent peak with expected isotope pattern), 239 (−27), 186 (some starting material) among others; $^1$H-nmr (trifluoroacetic acid) delta 7.5 ppm (starting material, s 0.1H), 9.3 (s, 1.0H). The nmr spectrum indicates that the reaction product is about 90% of the desired product; the remainder is starting material. This material is sufficiently pure for use in further reactions.

We claim:

1. A compound of the formula

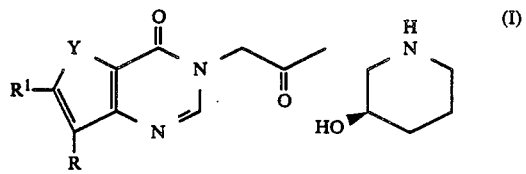

wherein Y is sulfur or oxygen; and

R and R$^1$ are taken separately, R is hydrogen, chloro or bromo and R$^1$ is chloro or bromo; or R and R$^1$ are taken together and are —CH=CH—CH=CH—; with the proviso that R and R$^1$ are taken together when Y is oxygen;

or a pharmaceutically acceptable acid addition salt thereof.

2. A compound of claim 1 wherein Y is sulfur.
3. A compound of claim 2 wherein R$^1$ is chloro.
4. The compound of claim 3 wherein R is hydrogen.
5. The compound of claim 3 wherein R is chloro.
6. The compound of claim 3 wherein R is bromo.
7. A compound of claim 1 wherein Y is oxygen.
8. The compound of claim 7 wherein R and R$^1$ are taken together and are —CH=CH—CH=CH—.
9. A method of controlling or preventing coccidiosis in poultry which comprises administering to said poultry an anticoccidially effective amount of a compound of claim 1 in drinking water or in nutritionally-balanced feed.
10. A method of controlling or preventing coccidiosis in poultry which comprises administering to said poultry an anticoccidially effective amount of a compound of claim 2 in drinking water or in nutritionally-balanced feed.

11. A method of controlling or preventing coccidiosis in poultry which comprises administering to said poultry an anticoccidially effective amount of a compound of claim 3 in drinking water or in nutritionally-balanced feed.

12. A method of controlling or preventing coccidiosis in poultry which comprises administering to said poultry an anticoccidially effective amount of the compound of claim 4 in drinking water or in nutritionally-balanced feed.

13. A method of controlling or preventing coccidiosis in poultry which comprises administering to said poultry an anticoccidially effective amount of the compound of claim 5 in drinking water or in nutritionally-balanced feed.

14. A method of controlling or preventing coccidiosis in poultry which comprises administering to said poultry an anticoccidially effective amount of the compound of claim 6 in drinking water or in nutritionally-balanced feed.

15. A method of controlling or preventing coccidiosis in poultry which comprises administering to said poultry an anticoccidially effective amount of a compound of claim 7 in drinking water or in nutritionally-balanced feed.

16. A method of controlling or preventing coccidiosis in poultry which comprises administering to said poultry an anticoccidially effective amount of the compound of claim 8 in drinking water or in nutritionally-balanced feed.

* * * * *